United States Patent
Öhrlein et al.

(10) Patent No.: US 7,507,853 B2
(45) Date of Patent: Mar. 24, 2009

(54) PROCESS FOR THE PREPARATION OF PHENOLIC CARBOXYLIC ACID DERIVATIVES BY ENZYMATIC CATALYSIS

(75) Inventors: Reinhold Öhrlein, Rheinfelden-Herten (DE); Gabriele Baisch, Binzen (DE); Kai-Uwe Schöning, Oberwil (CH); Jemima Schmidt, Schopfheim (DE); Sandra Franziska Mayer, Hetzendorf (AT)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 480 days.

(21) Appl. No.: 10/529,802

(22) PCT Filed: Oct. 2, 2003

(86) PCT No.: PCT/EP03/10967

§ 371 (c)(1),
(2), (4) Date: Mar. 30, 2005

(87) PCT Pub. No.: WO2004/033699

PCT Pub. Date: Apr. 22, 2004

(65) Prior Publication Data

US 2006/0110807 A1 May 25, 2006

(30) Foreign Application Priority Data

Oct. 10, 2002 (EP) .................................. 02405869

(51) Int. Cl.
C12P 7/42 (2006.01)
C12P 7/62 (2006.01)
C12P 7/22 (2006.01)
C12P 13/02 (2006.01)
C07C 69/88 (2006.01)
C07C 69/76 (2006.01)

(52) U.S. Cl. .............................. 560/67; 560/65; 560/75; 560/55; 560/87; 560/89; 560/95

(58) Field of Classification Search .................... 560/67
See application file for complete search history.

(56) References Cited

U.S. PATENT DOCUMENTS

| 4,594,444 A | 6/1986 | Orban ......................... 560/67 |
| 5,892,097 A | 4/1999 | Ross et al. ..................... 560/75 |
| 6,248,899 B1 | 6/2001 | Pugin et al. .................. 548/261 |
| 6,444,848 B1 | 9/2002 | Broussard et al. ........... 564/148 |

FOREIGN PATENT DOCUMENTS

| EP | 0808818 | 11/1997 |
| WO | 98/28256 | 7/1998 |
| WO | 00/34227 | 6/2000 |

OTHER PUBLICATIONS

H. Stamatis et al., Journal of Molecular Catalysis B: Enzymatic, vol. 11, (2001), pp. 323-328.
B. Guyot et al., Biotechnology Letters, vol. 19, No. 6, Jun. 1997, pp. 529-532.

*Primary Examiner*—Venkataraman Balasubramanian
(74) *Attorney, Agent, or Firm*—Shiela A. Loggins

(57) ABSTRACT

The present invention relates to an improved process for the preparation of phenolic carboxylic acid derivatives catalysed by biocatalytic esterification, transesterification or amidation of a corresponding lower alkyl ester. Biocatalysis is performed in the presence of suitable enzymes, e.g. hydrolases, especially esterases, amidases, lipases and proteases.

10 Claims, No Drawings

PROCESS FOR THE PREPARATION OF PHENOLIC CARBOXYLIC ACID DERIVATIVES BY ENZYMATIC CATALYSIS

The invention pertains to an improved process for the preparation of phenolic carboxylic acid derivatives catalysed by enzymatic esterification or amidation of the corresponding free acid or the lower alkyl ester.

So-called sterically hindered 3-hydroxyphenylpropionic acid esters and certain amide derivatives are well known as effective antioxidants for a wide variety of organic substrates, particularly lubricants and polymers, protecting them from oxidative and thermal degradation. Many of these esters have gained wide commercial acceptance as phenolic antioxidants. So-called sterically hindered 3-hydroxyphenylpropionic acid esters substituted at the phenyl ring by tert-butyl and a benzotriazolyl group are known as efficient UV-absorber molecules.

Transesterification reactions of carboxylic esters can be generally described by the following reaction scheme:

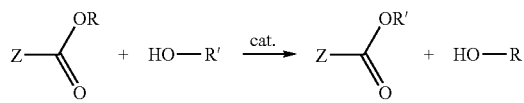

in which Z is an organic radical, R is a lower alkyl radical and $R^1$ is an ester group of higher chain length. The reaction is an equilibrium reaction. In general, the lower-boiling alcohol liberated is distilled off during the reaction. Various catalysts for this reaction are known (Junzo Otera, *Chem. Rev.*, 93 (1993) 1449-1470), e.g. acids, bases, amines, metal alkoxides and also, inter alia, organotin compounds. Many of these esterification reactions are carried out at higher temperatures in the range from 80° C. to above 200° C.

It is economically advantageous if the reactions can be carried out in the melt without the presence of solvents. Moreover, it is desirable that the product does not have to be purified in a subsequent distillation or extraction step. This excludes the use of so-called homogenous catalysts used in a solvent phase, such as aqueous solutions of acids or bases.

Suitable heterogeneous transesterification catalysts include lithium amide, aluminium isopropylate and dibutyltin oxide. U.S. Pat. No. 4,594,444 discloses a process for the preparation of sterically hindered 3-hydroxyphenylpropionic acid esters by the transesterification in the presence of an oxide or an organometallic compound of a metal of the fourth main group or transition metal group of the Periodic Table as catalyst in an amount between 0.05 and 1.0 mol percent based on the methyl or ethyl ester. Higher dialkyltin oxides, particularly dibutyltin oxides, are taught as the preferred catalyst for this process.

The formation of discoloured or stained products resulting from the presence of catalyst residues reaction is extremely undesirable. Certain desirable product properties, such as stability, or low toxicity, are negatively influenced in the presence of catalyst residues. Therefore, the removal of catalyst residues is highly desirable. Even though various references disclose a process, wherein the amount of tin catalyst is reduced, the problem of a complete removal of tin catalysts remains unsolved. Even low amounts of residual catalysts may interfere during final application and lead to undesired discoloration or reduced heat or light stability of the product.

A possible solution for this problem is the use of immobilised tin catalysts that can be separated off more easily. U.S. Pat. No. 5,436,357 discloses catalysts bound to polystyrene. These compounds are proposed as catalysts for transesterification in a lower temperature range from 50-1 50° C. They can be decanted or filtered off and used again. WO 98/28256 discloses a process for the transesterification of carboxylic esters, wherein the catalyst used is a tin(IV) compound comprising a radical of the formula:

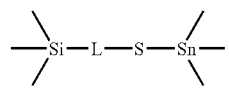

bound to an inorganic support, wherein L is an at least divalent radical and at least one of the free valences of the Si in the above partial formula is bound to the inorganic support.

These prior art processes require the attachment of tin catalysts to support molecules in a separate step preceding the transesterification reaction. It has surprisingly been found that biocatalysts are suitable catalysts that can be separated off directly from a melt or the reaction mixture without prior attachment to a support base.

The present invention relates to a process for the preparation of a compound of the formula:

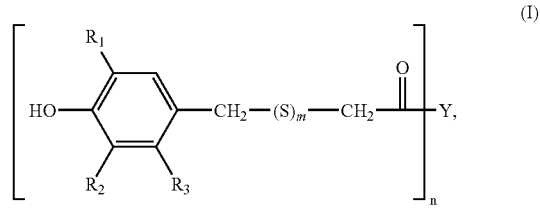

wherein
one of $R_1$ and $R_2$ independently of one another represents hydrogen, a substituent selected from the group consisting of $C_1$-$C_{18}$alkyl, phenyl, $(C_1$-$C_4$alkyl$)_{1-3}$phenyl, phenyl-$C_1$-$C_3$alkyl, $(C_1$-$C_4$alkyl$)_{1-3}$phenyl-$C_1$-$C_3$alkyl, $C_5$-$C_{12}$cycloalkyl and $(C_1$-$C_4$alkyl$)_{1-3}C_5$-$C_{12}$cycloalkyl or a group of the partial formula:

wherein
$R_a$ represents hydrogen or a substituent selected from the group consisting of $C_1$-$C_4$alkyl, halogen and sulpho;
and the other one of $R_1$ and $R_2$ represents a substituent selected from the group consisting of $C_4$-$C_{18}$alkyl, phenyl, $(C_1$-$C_4$alkyl$)_{1-3}$phenyl, phenyl-$C_1$-$C_3$alkyl, $(C_1$-$C_4$alkyl$)_{1-3}$phenyl-$C_1$-$C_3$alkyl, $C_5$-$C_{12}$cycloalkyl and $(C_1$-$C_4$alkyl$)_{1-3}C_5$-$C_{12}$cycloalkyl or a group of the partial formula (A);
$R_3$ represents hydrogen or methyl;
m represents zero or 1; and
n represents a numeral from 1 to 4; and,
if n represents 1, m represents zero or 1, Y represents the monovalent groups —O—$Y_1$ or —N(—$Y_2$)$_2$, wherein $Y_1$ is selected from the group consisting of $C_5$-$C_{45}$alkyl, $C_3$-$C_{45}$alkyl interrupted by at least one O-heteroatom, $C_5$-$C_{12}$cycloalkyl, $C_2$-$C_{12}$alkenyl,

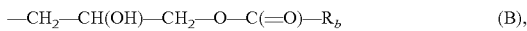  (B), wherein $R_b$ represents hydrogen or a substituent selected from the group consisting of $C_1$-$C_8$alkyl, $C_3$-$C_5$alkenyl and benzyl and

  (C), wherein $R_c$ represents hydrogen or a substituent selected from the group consisting of $C_1$-$C_{24}$alkyl, $C_5$-$C_{12}$cycloalkyl, phenyl,

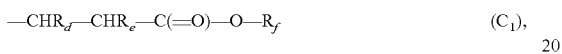  ($C_1$), wherein one of $R_d$ and $R_e$ represents methyl and the other one represents methyl and $R_f$ represents hydrogen or $C_1$-$C_{24}$alkyl,

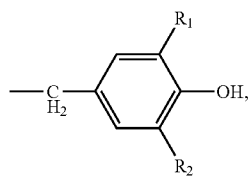  ($C_2$)

wherein $R_1$ and $R_2$ are as defined above, and

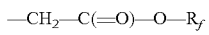  ($C_3$), wherein $R_f$ is as defined above; and
$Y_2$ represents hydroxy-$C_2$-$C_4$alkyl;
if n represents 2,
m represents zero, Y represents a bivalent group selected from the group consisting of

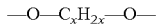  (D), wherein x is a numeral from 2 to 20,

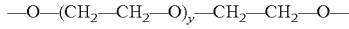  (E), wherein y is a numeral from 1 to 30,

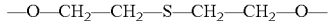  (F),

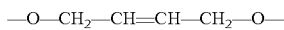  (G); and

  (H), wherein z represents zero or a numeral from 2 to 10; and
if n represents 3,
m represents zero and Y represents a trivalent group selected from the group consisting of

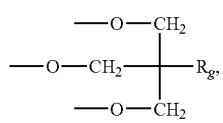  (K)

wherein $R_g$ represents $C_1$-$C_{24}$alkyl or phenyl, and

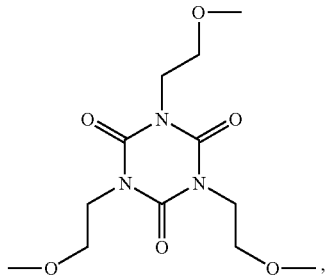  (L)

and, if n represents 4,
m represents zero and Y represents a tetravalent group of the partial formula:

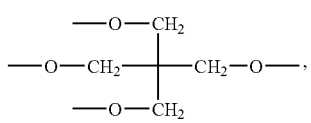  (M)

characterised in that in a compound of the formula:

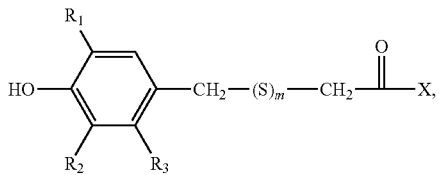  (II)

wherein
$R_1$, $R_2$, $R_3$, and m are as defined above and —X represents a reactive leaving group, the group —X is replaced by enzymatic catalysis with a mono-, bi-, tri- or tetravalent group —Y that corresponds to the value of the numeral n,
if n represents 1 with the monovalent groups —O—Y, or —N(—$Y_2$)$_2$; or,
if n represents 2, with one of the bivalent groups (D), (E), (F), (G) or (H); or,
if n represents 3, with one of the trivalent groups (K) or (L); or,
if n represents 4, with the tetravalent group (M).

The enzymatically catalysed esterification, transesterification or amidation process according to the present invention operates under mild conditions, such as low temperatures and under neutral or nearly neutral pH conditions. After completing the reaction the biocatalysts used can be separated from the reaction product simply and completely by known solid/liquid separation operations, for example filtration, centrifugation or decantation. The biocatalysts that have been filtered off remain catalytically active and may be reused a number of times, particularly in continuous processes.

The compounds (I) obtainable by the process according to the present invention are, for example, valuable antioxidants against oxidative, thermal or actinic degradation of organic compositions of matter. Such compositions are, for example, natural or synthetic polymers, functional liquids, such as lubricants, hydraulic fluids or metalworking fluids, etc. Some compounds (I) substituted at the phenyl ring by a tert-butyl and a benzotriazolyl group are known as efficient UV-absorber molecules.

The terms and definitions used in the description of the present invention preferably have the following meanings:

The various alkyl groups defined above of different chain length comprise saturated linear or, where possible, branched hydrocarbon groups, particularly $C_1$-$C_9$alkyl, e.g. methyl, ethyl, isopropyl, n-butyl, isobutyl, tert-butyl, n-pentyl, neopentyl, isopentyl, n-hexyl, 2-ethylbutyl, 1-methylpentyl, 1,3-dimethylbutyl, n-heptyl, 3-heptyl, 1-methylhexyl, isoheptyl, n-octyl, 2-ethylhexyl, 1,1,3,3-tetramethylbutyl, 1-methylheptyl, n-nonyl or 1,1,3-trimethylhexyl, as well as $C_{10}$-$C_{45}$alkyl, particularly straight chained $C_{10}$-$C_{45}$alkyl, e.g. n-decyl, n-dodecyl, n-tetradecyl, n-hexadecyl, n-octadecyl, icosyl, henicosyl, docosyl or triacontyl, or branched $C_{10}$-$C_{22}$alkyl, e.g. 1,1,3-trimethylhexyl, 1-methylundecyl, 2-n-butyl-n-octyl, isotridecyl, 2-n- hexyl-n-decyl or 2-n-octyl-n-dodecyl, or higher homologues thereof.

$(C_1$-$C_4$Alkyl$)_{1-3}$phenyl is, for example, 2- or 4-tolyl, 2,5- or 2,6-xylyl, mesityl, 2- or 4-ethylphenyl, 2,4- or 2,6-diethylphenyl, 4-cumenyl, 2-tert-butyl-6-methylphenyl or 2,6-bis-tert-butyl.

Phenyl-$C_1$-$C_3$alkyl is, for example, phenyl attached to $C_1$-$C_3$alkyl in 1-, 2- or 3-position, e.g. 2-phenylethyl, particularly benzyl.

$(C_1$-$C_4$Alkyl$)_{1-3}$phenyl-$C_1$-$C_3$alkyl is one of the above mentioned $(C_1$-$C_4$alkyl$)_{1-3}$phenyl attached to $C_1$-$C_3$alkyl in 1-, 2- or 3-position, e.g. 2-tert-butyl-6-methylbenzyl or 2,6-bis-tert-butyl-phenyl.

$C_5$-$C_{12}$Cycloalkyl is, for example, cyclopentyl or cyclohexyl.

$(C_1$-$C_4$Alkyl$)_{1-3}C_5$-$C_{12}$cycloalkyl is one of the above-mentioned $C_5$-$C_{12}$cycloalkyl groups substituted with 1-3 $C_1$-$C_4$alkyl, e.g. 2- or 4-methylcyclohexyl, 2,6-dimethylcyclohexyl, 2,4,6-trimethylcyclohexyl or 4-tert-butylcyclohexyl.

Alkenyl of different chain length is, for example, vinyl, allyl, 2-butenyl, methallyl, 2- or 3-hexenyl, or 3- or 5-decenyl.

The partial formula (A) comprises within its scope the following isomer:

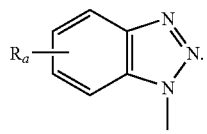
(A')

$R_a$ defined as halogen is bromo or iodo, particularly chloro.

In a compound (I), the numeral m represents zero or one. In the event that m represents zero, the direct bond is defined. In an alternative embodiment the numerals m and n represent 1 and Y represents the monovalent group —O—$Y_1$. Compounds (I) of this type are represented by the formula:

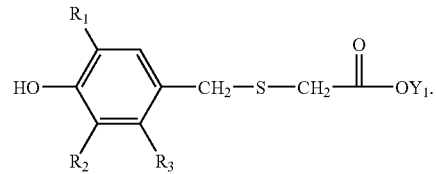
(Ia)

$Y_1$ defined as $C_3$-$C_{45}$alkyl interrupted by at least one —O—heteroatom comprises the above mentioned $C_3$-$C_{45}$alkyl groups, preferably 2-methoxyethyl, 2- or 3-methoxypropyl, 2-, 3- or 4-methoxybutyl, 2-ethoxyethyl, 2- or 3-ethoxypropyl, 2-, 3- or 4-ethoxybutyl, 2-n-propoxyethyl, 2- or 3-n-propoxypropyl, 2-, 3- or 4-n-propoxybutyl, 2-isopropoxyethyl, 2- or 3-isopropoxypropyl, 2-, 3- or 4-isopropoxybutyl, 2-n-butoxyethyl, 2- or 3-n-butoxypropyl, 2-, 3- or 4-n-butoxybutyl, 2-tert-butoxyethyl, 2- or 3-tert-butoxypropyl, 2-, 3- or 4-tert-butoxybutyl and higher homologues, particularly linear $C_5$-$C_{18}$alkyl substituted with methoxy, ethoxy, n-propoxy, isopropoxy or tert-butoxy.

$R_b$ in a group of the partial formula (A) is preferably hydrogen, allyl, methallyl or benzyl.

$R_c$ in a group of the partial formula (C) is preferably hydrogen or $C_1$-$C_4$alkyl.

Y2 defined as hydroxy-$C_2$-$C_4$alkyl is preferably 2-hydroxyethyl.

A particularly preferred group of compounds (I), wherein m is zero and represents the direct bond and n is one, is represented by the general formulae:

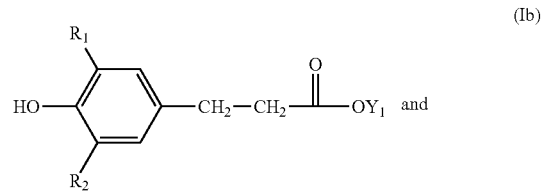
(Ib)

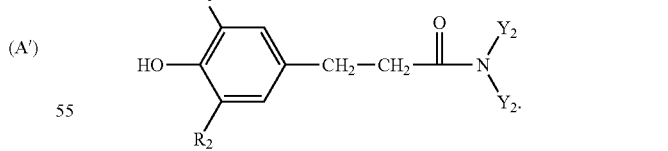
(Ic)

In these compounds one of $R_1$ and $R_2$ represents methyl or tert-butyl and the other one represents tert-butyl, $Y_1$ represents straight chained or branched $C_{10}$-$C_{22}$alkyl and $Y_2$ represents 2-hydroxyethyl.

Another particularly preferred group of compounds (I), wherein m is zero and represents the direct bond and n is one, is represented by the general formula:

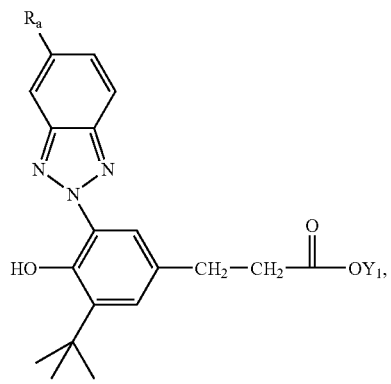
(Id)

wherein $R_a$ represents hydrogen or chloro and $Y_1$ represents straight chained or branched $C_{10}$-$C_{22}$ alkyl.

A preferred alternative embodiment relates to the preparation of compounds (1), wherein n represents 2, m represents zero, Y represents a bivalent group selected from the group consisting of $$—O—C_xH_{2x}—O— \quad (D),$$

wherein x is a numeral from 2 to 20, $$—O—(CH_2—CH_2—O)_y—CH_2—CH_2—O— \quad (E),$$

wherein y is a numeral from 1 to 30, $$—O—CH_2—CH_2—S—CH_2—CH_2—O— \quad (F),$$

$$—O—CH_2—CH=CH—CH_2—O— \quad (G); \text{ and}$$

$$—NH—(CH_2)_z—NH— \quad (H),$$

wherein z represents zero or a numeral from 2 to 10. Preferred compounds are represented by the formulae:

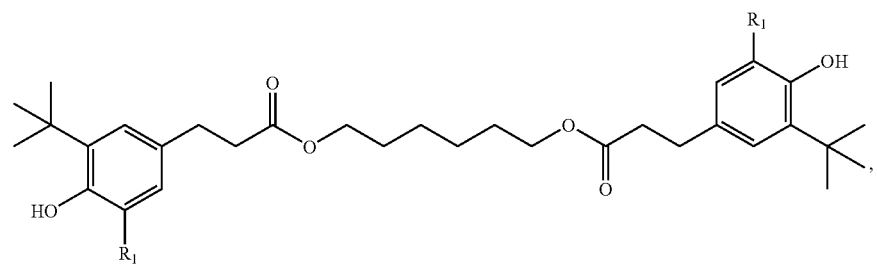

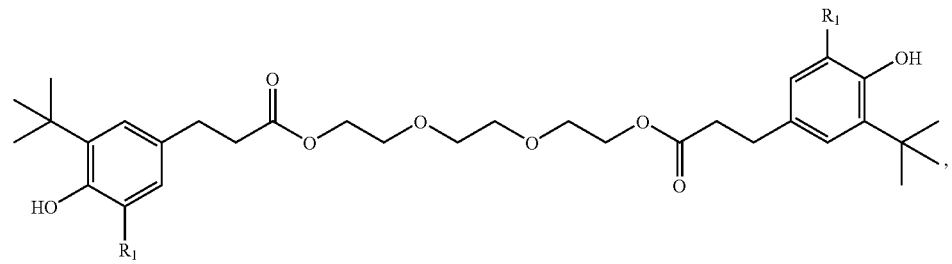

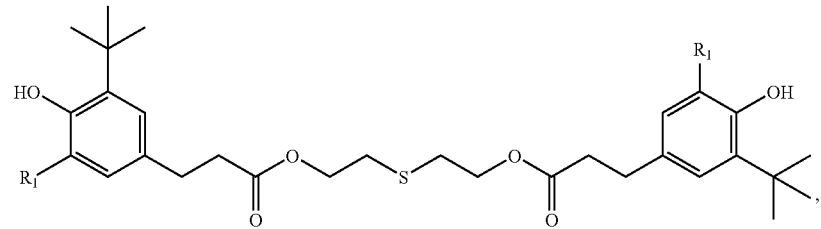

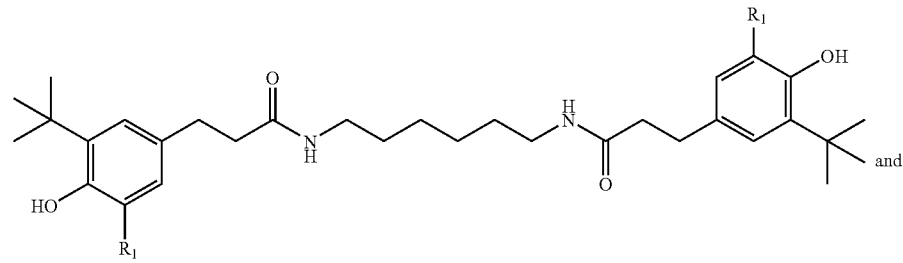

and

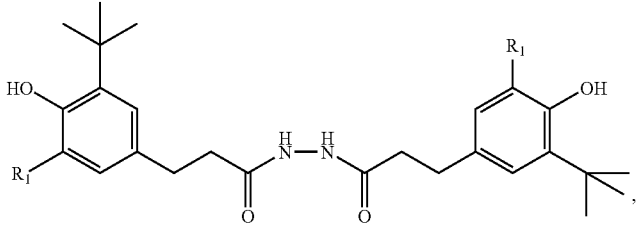

wherein R₁ represents hydrogen or tert-butyl.

Another preferred alternative embodiment relates to the preparation of compounds (I), wherein n represents 3, m represents zero and Y represents the trivalent group:

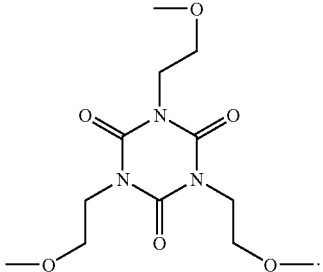

(L)

Such compound is represented by the formula:

Another preferred alternative embodiment relates to the preparation of compounds (I), wherein n represents 4 and m represents zero.

Such compound is represented by the formula:

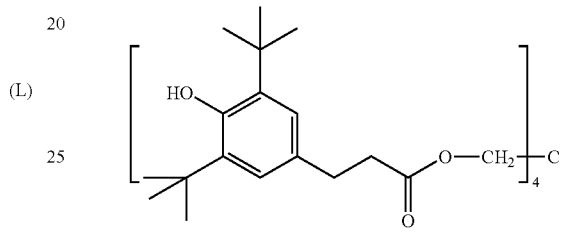

A preferred embodiment of the invention relates to a process for the preparation of a compound (I), wherein
one of $R_1$ and $R_2$ represents methyl, tert-butyl or the group (A), wherein $R_a$ represents hydrogen or chloro, and the other one of $R_1$ and $R_2$ represents tert-butyl;
$R_3$ represents hydrogen;
m represents zero or 1; and
n represents a numeral from 1 to 4; and,
if n represents 1, m represents zero or 1, and Y represents the monovalent groups —O—$Y_1$ or —N(—$Y_2$)$_2$; or

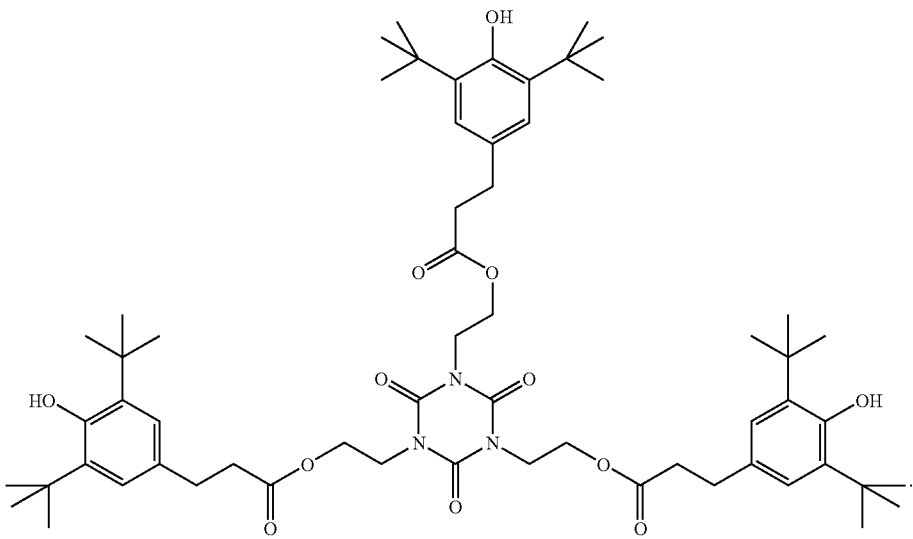

if n represents 2, m represents zero, and Y represents the bivalent groups (D), (E), (F), (G) or (H); or, if n represents 3, m represents zero, and Y represents the trivalent group of the partial formulae (K) or (L); or, if n represents 4, m represents zero, and Y represents the tetravalent group of the partial formula (M).

A particularly preferred embodiment of the invention relates to a process for the preparation of a compound (I), wherein one of $R_1$ and $R_2$ represents methyl, tert-butyl or the group (A), wherein $R_a$ represents hydrogen or chloro, and the other one of $R_1$ and $R_2$ represents tert-butyl;

$R_3$ represents hydrogen;

m represents zero or 1; and n represents a numeral from 1 to 4; and, if n represents one, m represents zero or one, and Y represents the monovalent groups —O—$Y_1$ or —N(—$Y_2$)$_2$;

wherein $Y_1$ is selected from the group consisting of $C_5$-$C_{45}$alkyl and $C_3$-$C_{45}$alkyl interrupted by at least one O-heteroatom and $Y_2$ represents hydroxy-$C_2$-$C_4$alkyl; and, if n represents 2, m represents zero, Y represents a bivalent group selected from the group consisting of

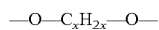   (D), wherein x is a numeral from 2 to 20,

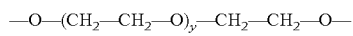   (E), wherein y is a numeral from 1 to 30,

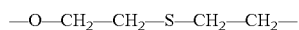   (F),

   (H);

wherein z represents zero or a numeral from 2 to 10; and, if n represents 3, m represents zero and Y represents a trivalent group selected from the group consisting of

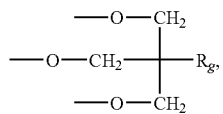   (K)

wherein $R_9$ represents $C_1$-$C_{24}$alkyl, and

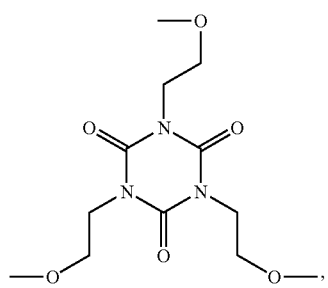   (L)

and, if n represents 4, m represents zero and Y represents a tetravalent group of the partial formula:

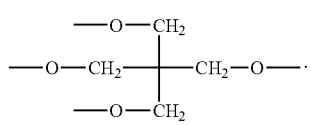   (M)

A highly preferred embodiment of the invention relates to a process for the preparation of a compound (I), wherein one of $R_1$ and $R_2$ represents methyl, tert-butyl or the group (A), wherein $R_a$ represents hydrogen or chloro, and the other one of $R_1$ and $R_2$ represents tert-butyl;

$R_3$ represents hydrogen;

m represents zero or 1; and n represents a numeral from 1 to 4; and, if n represents one, Y represents the monovalent groups —O—$Y_1$ or —N(—$Y_2$)$_2$;

wherein $Y_1$ is selected from the group consisting of $C_5$-$C_{20}$alkyl and $C_3$-$C_{20}$alkyl interrupted by at least one O-heteroatom and $Y_2$ represents hydroxy-$C_2$-$C_4$alkyl; and, if n represents 2, m represents zero, Y represents a bivalent group selected from the group consisting of

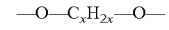   (D), wherein x is a numeral from 2 to 10,

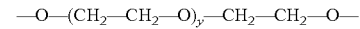   (E), wherein y is a numeral from 1 to 10,

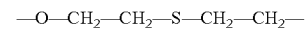   (F),

   (H);

wherein z represents zero or a numeral from 2 to 10; and, if n represents 3, m represents zero, and Y represents the trivalent group (L); and, if n represents 4, m represents zero and Y represents a tetravalent group (M).

Another highly preferred embodiment of the invention relates to a process for the preparation of a compound (I), wherein one of $R_1$ and $R_2$ represents methyl or tert-butyl and the other one of $R_1$ and $R_2$ represents tert-butyl;

R3 represents hydrogen;

m represents zero or 1; and n represents a numeral from 1 to 4; and, if n represents 1, Y represents the monovalent groups —O—$Y_1$ or —N(—$Y_2$)$_2$;

wherein $Y_1$ is selected from the group consisting of $C_5$-$C_{20}$alkyl and $C_3$-$C_{20}$alkyl interrupted by at least one O-heteroatom and $Y_2$ represents hydroxy-$C_2$-$C_4$alkyl; and, if n represents 2, m represents zero, Y represents a bivalent group selected from the group consisting of

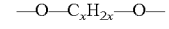   (D), wherein x is a numeral from 2 to 10,

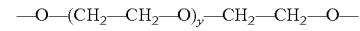   (E), wherein y is a numeral from 1 to 10,

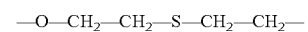   (F),

   (H);

wherein z represents zero or a numeral from 2 to 10; and,
if n represents 3,
m represents zero, and Y represents the trivalent group (L); and, if n represents 4, m represents zero and Y represents a tetravalent group (M).

A most preferred embodiment of the invention relates to a process for the preparation of a compound (I), wherein
$R_1$ represents tert-butyl;
$R_2$ represents the group (A), wherein $R_a$ represents hydrogen;
$R_3$ represents hydrogen;
m represents zero;
n represents 1; and
Y represents the monovalent group —O—$Y_1$;
wherein $Y_1$ is selected from the group consisting of $C_5$-$C_{20}$alkyl and $C_3$-$C_{20}$alkyl interrupted by at least one O-heteroatom.

The process steps of the preferred embodiments are described below. The inventive process comprises the following steps:

In a compound of the formula (II), wherein $R_1$, $R_2$, $R_3$ and m are as defined above, the reactive leaving group —X is replaced by enzymatic catalysis with a mono-, bi-, tri- or tetravalent group —Y that corresponds to the value of the numeral n,
if n represents 1 with the above-mentioned monovalent groups —O—$Y_1$ or —N(—$Y_2$)2; or,
if n represents 2, with one of the above-mentioned bivalent groups (D), (E), (F), (G) or (H); or,
if n represents 3, with one of the above-mentioned trivalent groups of the partial formula (K) or (L); or,
if n represents 4, with the above-mentioned tetravalent group of the partial formula (M).

The removal of the reactive leaving group —X and replacement with a different group —Y is a common feature in so-called esterification, particularly transesterification, and transamidation reactions. A suitable reactive leaving group —X is, for example the hydroxy or $C_1$-$C_4$alkoxy group, particularly methoxy.

Enzymatic catalysis according to the process of the present invention is performed in the presence of a suitable biocatalyst, such as enzymes, e.g. hydrolases, especially esterases, amidases, lipases and proteases, such as the ones described in *Hydrolases in Organic Synthesis; Wiley-VCH* (U. T. Bornscheuer, R. T. Kazlauskas) 1999, pages 65-195, ISBN 3-527-30104-6. Specific examples of esterases are those obtained from the intestines of warm-blooded animals, such as horse liver esterase, porcine liver esterase or porcine pancreas lipase (PPL), fungal esterases or esterases from microorganisms, such as *Bacillus subtilis, Pichia polimorpha Rhizopus* sp. or *Penicillium* sp. or yeast esterases.

Suitable lipases include those of animal, plant and microbiological origin, particularly those found in many strains of bacteria and fungi, such as esterases from *Candida, Alcaligene* species or *Pseudomonas* species, such as *Amano P* or the lipase from *Pseudomonas* spec DSM 8246. Specific examples are *Aspergillus niger* (Amono AP6). *G. candidum* (GCL), *H. lanuginosa* (HLL). *Rhizopus* sp. (RML, ROL), *Candida* sp. (CCL), such as the ones from *Candida antarctica* (CAL-A, CAL-B), *Aspergillus* sp. (ANL), *Pseudomonas* sp. (PCL, PFL). Suitable enzymes are proteolytic enzymes, too, such as subtilisin, thermitase, chymotrypsin, thermolysin, papain, aminoacylase, penicillin amidase or trypsin. Suitable enzymes are known to those skilled in the art and are not limited to the ones mentioned above.

The enzymes can be employed as crude extracts, in pure form or in immobilised crude or pure form, particularly on a support or carrier, to which they are linked chemically or physically. Suitable supports, are for example, silica gel, diatomite, Celite®, Eupergit® (Röhm & Haas, Darmstadt, Germany) and the like. Such methods are described by W. Tischer et al. *TIBTECH* 1999, 17, 326; J. Lalonde, *Curr. Oin. Drug Disc. & Develop.* 1998, 1(3) 271.

The enzymes can also be employed as cross-linked-enzymes (CLEC's), which enzymes may be obtained from Altus Corp. Suitable enzymes are well known and are described, for example, in *Hydrolases in Organic Synthesis*; Wiley-VCH, loc. cit. pages 61-64, *Biotransformation in Organic Chemistry* (K. Faber), *Springer Verl.* 1997, $3^{rd}$ Ed., pages 345-357, ISBN 3-540-61688-8; *Biotechnology* (H.-J. Rehm, G. Reed), VCH 1998, $2^{nd}$ Ed. Pages 407-411.

Preferred are enzymes that are commercially available, such as the hydrolases available from Novo Nordisk (Enzyme Toolbox), particularly the lipases SP 523, 524, 525 and 526 and Novozyme®435 (recombinant *Candida antarctica* lipase B (E. M. Anderson et al. *Biocat. Biotransf.* 1998, 16 181)), NOVO Nordisk, Bagswaerd, Denmark) or the enzyme QLM, QL (Meito Sangyo, Japan) or enzymes that are well known and described, e. g. by H.-J. Rehm and G. Reed in *Biotechnology, loc. cit.,* pages 40-42).

Especially preferred are immobilised lipases that are thermostable, such as Rhizomucor miehei immobilised lipase (Lipozyme®) or NOVOZYME 435.

Enzymes having esterase, lipase and/or protease activity may be obtained from natural sources and/or from microorganism using standard procedures known in the art, for example from cloning processes via expression and amplification. An alternative embodiment relates to the inclusion of the enzymatic biocatalyst in a semi-permeable membrane. This increases the stability of the biocatalyst and its separability from reagents, reactants and products. Reference is made to Enzymes in *Org. Chem.* (C.H. Wong, G. M. Whitesides editors), Pergamon Press 1994, ISBN 0-08-035941-8.

Another advantage is the suitability of the process according to the invention for a continuous process in an appropriate reaction vessel. Such methods are described by V. M. Balcao et al. *Enzyme Microbiol. Techn.* 1996, 18 392; L. Giorno et al. *TIBTECH* 2000, X, 339.

The instant enzymatic esterification, transesterification or amidation process is carried out at lower temperatures, especially from 10-80° C., preferably from 25- 60° C. The process can be carried out without adding a solvent. The presence of a solvent, such as hexane, toluene, benzene, THF, diethyl ether, methyl-tert-butyl ether, methylene chloride and the like is optional.

The amount-of the enzyme catalyst depends on the substrate used and on the reaction conditions, such as temperature, reaction time, solvent, but may be from 0.01 to 20.0% by weight, preferably from 1.0 to 10.0% by weight, based on the weight of the reactants.

The reaction time for performing the process depends on the amount of reactants used and on the activity of the enzyme catalyst, and amounts to, for example, 48 hours, preferably 24 hours.

In order to maximise the degree of conversion, the product HX formed in the process, in particular water or the lower alkanol is removed by routine methods, for example by vacuum distillation.

The reactive leaving group —X is replaced by enzymatic catalysis with a mono-, bi-, tri- or tetravalent group —Y. that corresponds to the value of the numeral n, in the presence of a suitable alcohol (esterification, transesterification) or a suitable amine (amidation).

If n represents 1, the esterification or transesterification is performed with the alcohol HO—Y, that corresponds to the monovalent groups —O—$Y_1$. The amidation is performed with an amine HN(—$Y_2$)$_2$ that corresponds to the group or —N(—$Y_2$)$_2$.

If n represents 2, the transesterification is performed with the alcohol selected from the group consisting of

  (D'), wherein x is a numeral from 2 to 20,

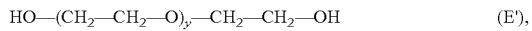  (E'), wherein y is a numeral from 1 to 30,

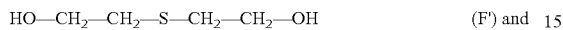  (F') and

  (G').

The amidation is performed with hydrazine, if z is zero, or with the diamine:

  (H'), if z is a numeral 2-10.

If n represents 3, the esterification or transesterification is performed with an alcohol corresponding to:

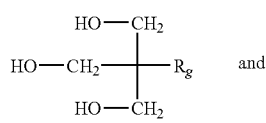  (K')

and

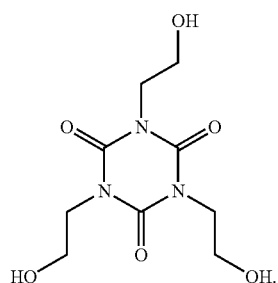  (L')

If n represents 4, the esterification or transesterification is performed with pentaerythritol C(CH$_2$OH)$_4$.

The above-mentioned esterification, transesterification or amidation processes generally require a time period from 1 to 10 hours, advantageously from 1 to 5 hours and preferably from 1 to 3 hours, to achieve optimum yields.

The biocatalyst can, for example, be present in the reaction mixture as a suspension of a powder. Use of the catalyst in a fixed bed is a preferred option of carrying out the process.

The present invention also relates to the reaction mixture, which consists of a composition comprising a) a compound (I), wherein $R_1$, $R_2$, $R_3$, m, n and Y are as defined above; and b) an enzyme catalyst that catalyses in a compound (II) the removal of the reactive leaving group —X with a mono-, bi-, tri- or tetravalent group —Y.

Additional components of the composition optionally present in the composition are the above-mentioned compounds (II), e.g. as unreacted reactants, and the above-mentioned solvents.

After finishing the biocatalysed reaction, the enzyme catalyst can be separated off by known methods, such as filtration or decantation, and used a number of times. The products (I) obtained by the process according to the invention and the reactants (II) are known or can be obtained by methods known per se.

The products prepared by the process according to the invention are, for example, useful antioxidants against oxidative, thermal or actinic degradation of degradable organic substrates. Suitable substrates are, for example, synthetic or natural polymers or functional fluids, such as lubricants, hydraulic fluids or metalworking fluids, etc.

The products obtained by the novel and inventive process as described above are also subject matter of the invention.

The following Examples illustrate the invention:

Abbreviation
TLC: thin layer chromatography

EXAMPLE 1

Preparation of

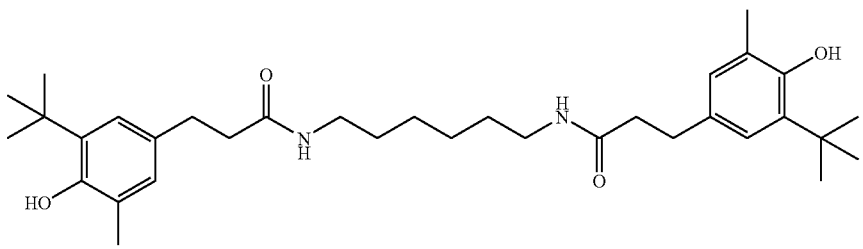

One equivalent (0.3 g) 1,6-hexanediamine (Acros/ www.acros.be), 8 equivalents (5.17 g) 3-(3-tert-butyl-4-hydroxy-5-methyl-phenyl)-propionic acid methyl ester and 1.5 g enzyme (Novozyme® 435) are stirred without solvent at 70° C. After completion of the reaction (check with TLC) and addition of 40 ml MeOH the resulting mixture is filtered through a plug of Celite® 501 to remove the biocatalyst. After evaporating the solvent the residue is purified by flash chromatography (hexane/EtOAc, 1:1), and the compound of the above formula is obtained.

EXAMPLE 2

Preparation of

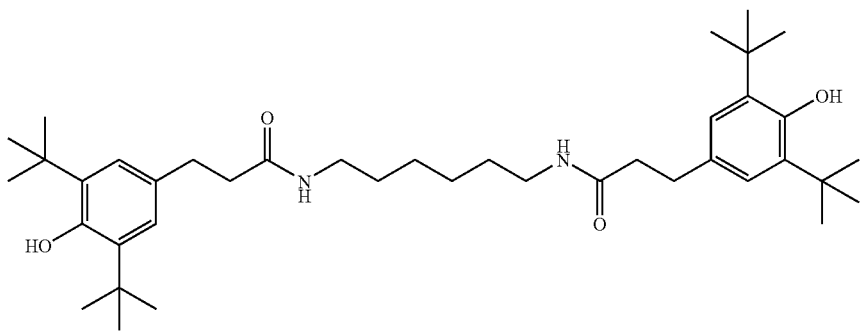

This compound is obtained in a manner analogous to Example 1 from 8 equivalents (6.04 g) 3-(3,5-di-tert-butyl-4-hydroxyphenyl)-propionic acid methyl ester.

EXAMPLE 3

Preparation of

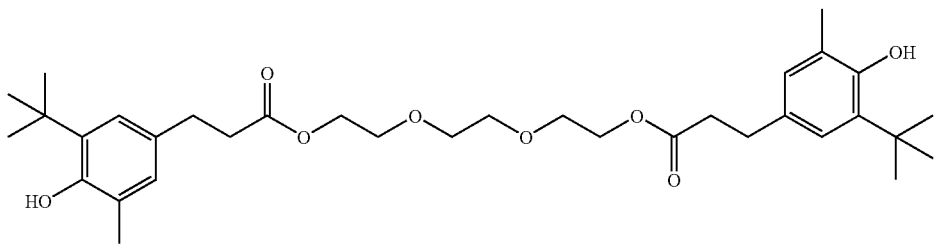

5.00 g 3-(5-tert-Butyl4-hydroxy-3-methylphenyl)-propionic acid methyl ester are heated to 70° C. at 0.1 mbar under vigorous stirring with 0.6 g triethylene glycol und 0.5 g RM IM (R. miehei)-Lipase (NOVO) until complete removal of the triethylene glycol. The reaction mixture is washed after cooling to room temperature with methylene chloride. After removal of the solvent the product is obtained by distillation at 0.1 mbar/160° C. in a purity of 99.6%.

EXAMPLE 4

Preparation of

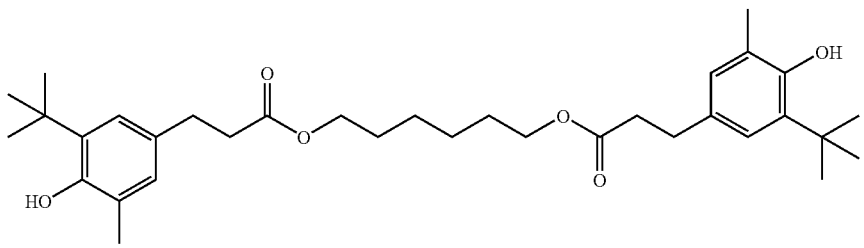

25.00 g 3-(5-tert-Butyl-4-hydroxy-3-methylphenyl)-propionic acid methyl ester are heated to 70° C. in 50 ml toluene at 150 mbar under vigorous stirring with 6.00 g hexane-1,6-diol and 10.0 g NOVO 435-Lipase (NOVO) until complete disappearance of the diol component. The reaction mixture is washed after cooling to room temperature with a methylene chloride and acetone mixture. After removal of the solvent the product is obtained by recrystallisation from methanol.

EXAMPLE 5

Preparation of

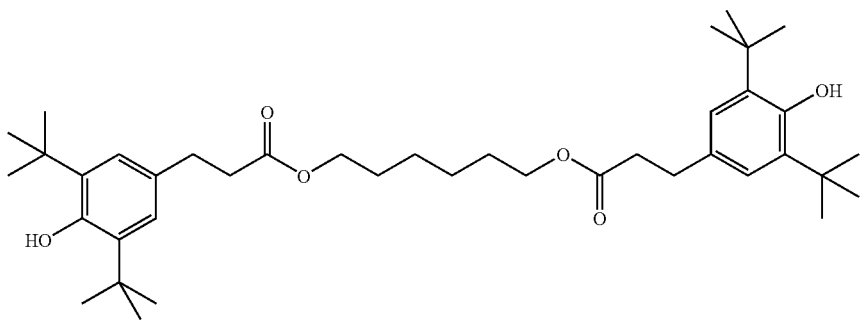

3.70 g 3-(3,5-Di-tert-butyl-4-hydroxyphenyl)-propionic acid methyl ester are heated to 70° C. in 50 ml toluene at 0.1 mbar under vigorous stirring with 0.50 g hexane-1,6-diol and 0.8 g NOVO 435-Lipase (NOVO) until complete disappearance of the diol component (ca. 24 h). The reaction mixture is washed with methylene chloride after cooling to room temperature. The product is obtained after removal of the solvent by sublimation at 0.1 mbar/90° C.

EXAMPLE 6

Preparation of

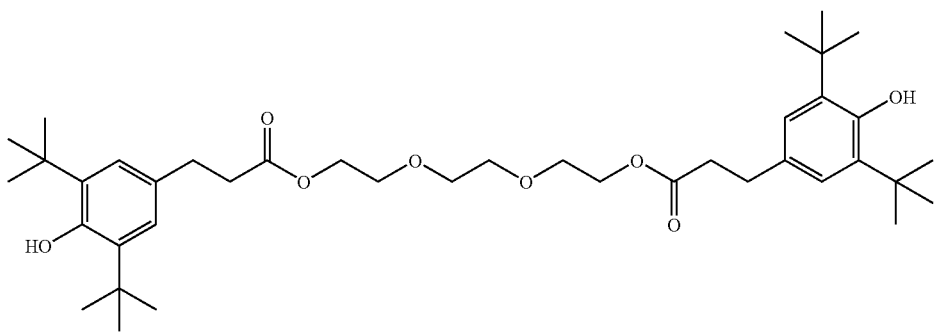

2.90 g 3-(3,5-Di-tert-butyl-4-hydroxyphenyl)-propionic acid methyl ester are heated to 70° C. in 50 ml toluene at 0.1 mbar under vigorous stirring with 0.5 g triethylene glycol and 0.8 g NOVO 435-Lipase (NOVO) until complete disappearance of the diol component (ca. 48 h). The reaction mixture is washed with methylene chloride after cooling to room temperature.

The reaction product is obtained by purification with silica gel (hexane/ ethyl acetate 10:4) and removal of the solvent.

EXAMPLE 7

Preparation of

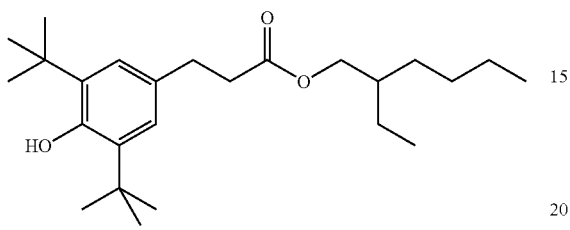

0.5 g 3-(3,5-Di-tert-butyl-4-hydroxyphenyl)-propionic acid methyl ester are heated to 70° C. in 3 ml toluene at 200 mbar under vigorous stirring with 0.27 g isooctanol and 0.3 g LIPOZYME RM IM (NOVO) until complete disappearance of the alcohol component (ca. 48 h). The reaction mixture is washed with methylene chloride after cooling to room temperature. After removal of the solvent at 0.1 mbar/90° C. the product is obtained as a residue.

EXAMPLE 8

Preparation of

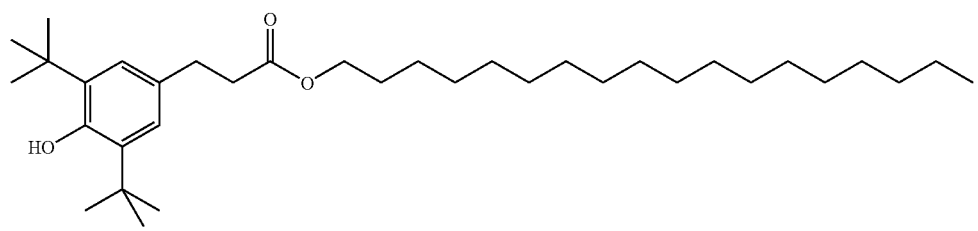

0.50 g 3-(3,5-Di-tert-butyl-4-hydroxyphenyl)-propionic acid methyl ester are heated to 70° C. in 3 ml toluene at 200 mbar under vigorous stirring with 0.55 g stearic alcohol and 0.3 g LIPOZYME RM IM (NOVO) until complete disappearance of the alcohol component (ca. 48 h). The reaction mixture is washed with methylene chloride after cooling to room temperature. After removal of the solvent the product is obtained as a residue.

EXAMPLE 9

Preparation of

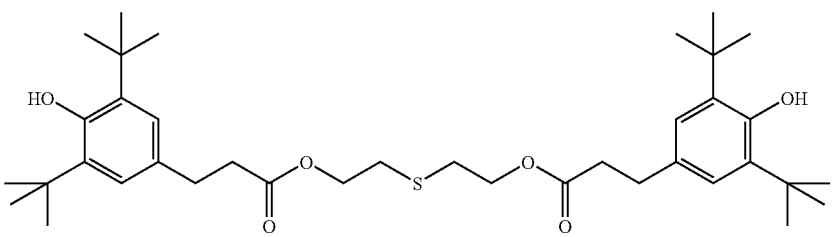

A melt of 5 equivalents 3-(3,5-di-tert-butyl4-hydroxyphenyl)-propionic acid methyl ester and 1 equivalent bis-(2-hydroxyethyl)sulphide is mixed with 5-10 wt. % NOVOZYME 435 are stirred at 200 mbar for 24 h at 70-80 ° C. After dissolving the reaction mixture in THF, filtering off the enzyme and distilling off the surplus of the ester component the product is obtained as the residue.

EXAMPLE 10

Preparation of

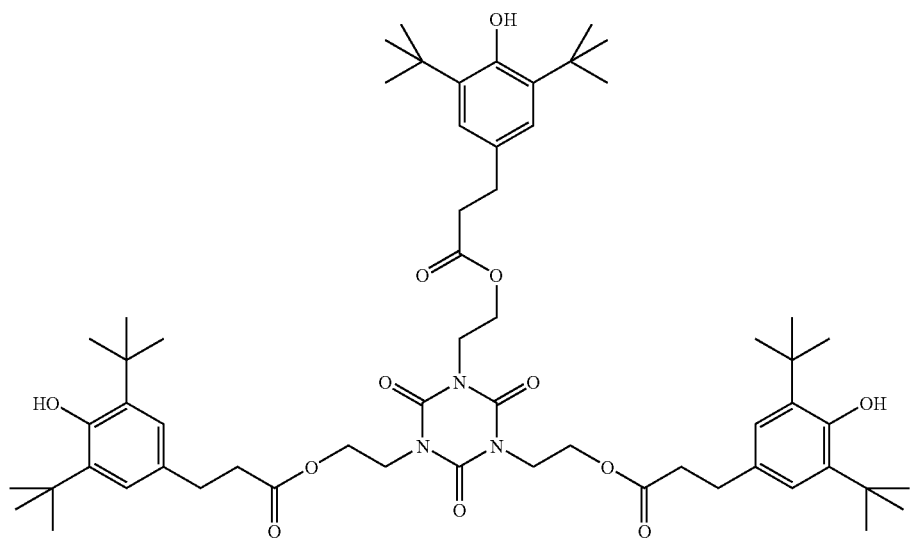

In a manner analogous to Example 9 the above compound is obtained from a melt of 1 equivalent 1,3,5-tris-(2-hydroxyethyl)-1,3,5-triazinane-2,4,6-trione und 10 equivalents 3-(3,5-di-tert-butyl-4-hydroxyphenyl)-propionic acid methyl ester with 5-10 wt. % LIPOZYME RM IM and removal of the surplus ester component.

EXAMPLE 11

Preparation of

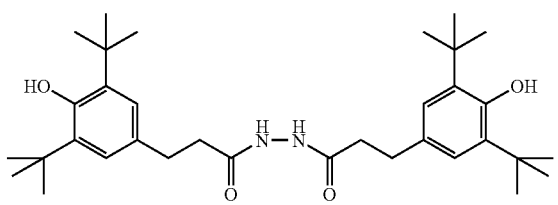

In a manner analogous to Example 9 the above compound is obtained from a melt of 1 equivalent hydrazine hydrate solution (24-26%) und 7-10 equivalents 3-(3,5-di-tert-butyl-4-hydroxy-phenyl)-propionic acid methyl ester with 5-10 wt % LIPOZYME RM IM and removal of the surplus ester component. The product is purified by crystallisation from xylene.

EXAMPLE 12

Preparation of

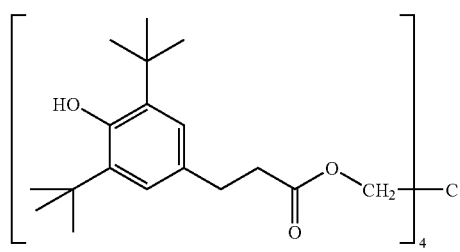

In a manner analogous to Example 9 the above compound is obtained from a melt of 10 equivalents 3-(3,5-di-tert-butyl4-hydroxyphenyl)-propionic acid vinyl ester and 1 equivalent pentaerythritol with 5-10 wt. % LIPOZYME TL IM and removal of the surplus ester component.

EXAMPLE 13

Preparation of

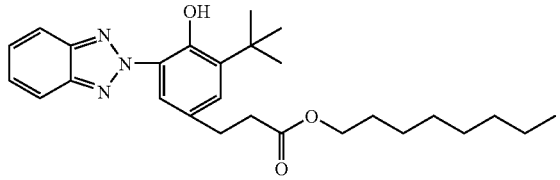

3-(3-Benzotriazole-2-yl-5-tert-butyl-4-hydroxyphenyl)-propionic acid methyl ester is dissolved in 10 equivalents 1-n-octanol and stirred at 60° C. and 500 mbar with 5 wt. % LIPOZYME RM IM or LIPOZYME TL IM 2-5 d. After removal of the solvent and the surplus ester component the pure product is obtained.

EXAMPLE 13

Preparation of

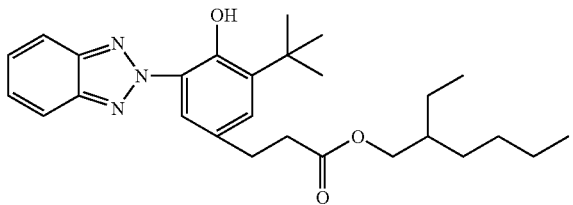

3-(3-Benzotriazole-2-yl-5-tert-butyl-4-hydroxyphenyl)-propionic acid methyl ester is dissolved in 10 equivalents 2-ethyl-1-hexanol and stirred at 60° C. and 500 mbar with 5 wt. % LIPOZYME RM IM or LIPOZYME TL IM 2-5 d. After removal of the solvent and the surplus ester component the pure product is obtained.

EXAMPLE 14

Preparation of

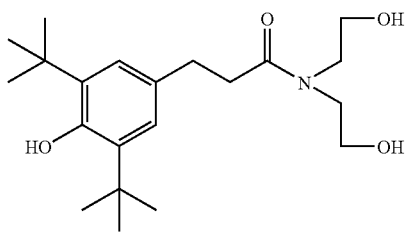

Eight equivalents (5.6 g) diethanolamine (Aldrich), 1 equivalent (1.1 g) 3-(3,5-di-tert-butyl-4-hydroxyphenyl)-propionic acid methyl ester and 1 g of enzyme (Novozyme® 435) are stirred at 80° C. After reacting 68 h (results of TLC) the reaction mixture is filtered through a plug of CELITE 501 to remove the biocatalyst and the solvent is evaporated. The residue is purified by Flash chromatography (hexane/EtOAc, 1:3).

EXAMPLE 15

Preparation of

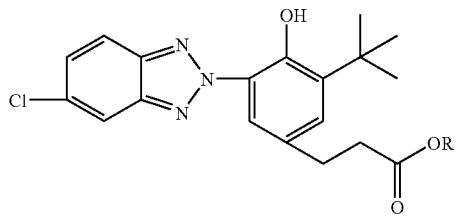

R = 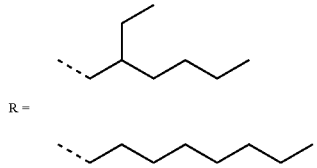

1 g 3-[5-tert-Butyl- 3-(5-chlorobenzotriazole-2-yl)4-hydroxyphenyl]-propionic acid methyl ester is dissolved in 10 ml a 1:1 mixture consisting of 1-octanol and 2-ethylhexanol. 1 g LIPOZYME TL IM is added and the mixture is stirred at 50° C. After three days the remaining solvents are removed and the 1:1 product mixture is obtained.

What is claimed is:
1. A process for the preparation of a compound of the formula:

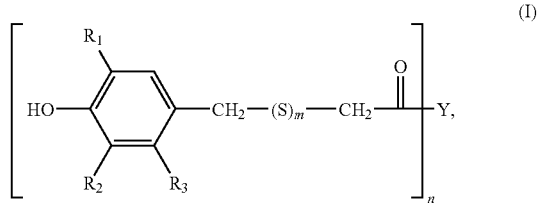

wherein
one of $R_1$ and $R_2$ independently of one another represents hydrogen, a substituent selected from the group consisting of $C_1$-$C_{18}$alkyl, phenyl, ($C_1$-$C_4$alkyl)$_{1-3}$phenyl, phenyl-$C_1$-$C_3$alkyl, ($C_1$-$C_4$alkyl)$_{1-3}$phenyl-$C_1$-$C_3$alkyl, $C_5$-$C_{12}$cycloalkyl and ($C_1$-$C_4$alkyl)$_{1-3}$$C_5$-$C_{12}$cycloalkyl or a group of the partial formula:

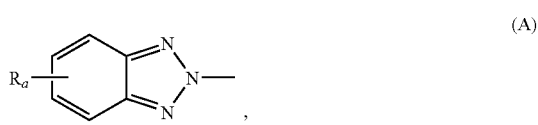

wherein
$R_a$ represents hydrogen or a substituent selected from the group consisting of $C_1$-$C_4$alkyl, halogen and sulpho;
and the other one of $R_1$ and $R_2$ represents a substituent selected from the group consisting of $C_4$-$C_{18}$alkyl, phenyl, ($C_1$-$C_4$alkyl)$_{1-3}$phenyl, phenyl-$C_1$-$C_3$alkyl, ($C_1$-$C_4$alkyl)$_{1-3}$phenyl-$C_1$-$C_3$alkyl, $C_5$-$C_{12}$cycloalkyl and ($C_1$-$C_4$alkyl)$_{1-3}$$C_5$-$C_{12}$cycloalkyl or a group of the partial formula (A);
$R_3$ represents hydrogen or methyl;
m represents zero or 1; and n represents a numeral from 1 to 4; and,
if n represents 1,
m represents zero or 1, Y represents the monovalent groups —O—$Y_1$ or —N(—$Y_2$)$_2$, wherein $Y_1$ is selected from the group consisting of $C_5$-$C_{45}$alkyl, $C_3$-$C_{45}$alkyl interrupted by at least one O-heteroatom, $C_5$-$C_{12}$cycloalkyl, $C_2$-$C_{12}$alkenyl, —CH$_2$—CH(OH)—CH$_2$—O—C(=O)—$R_b$ (B), wherein
$R_b$ represents hydrogen or a substituent selected from the group consisting of $C_1$-$C_8$alkyl, $C_3$-$C_5$alkenyl and benzyl and —CH$_2$—CH$_2$—O—$R_c$ (C), wherein
$R_c$ represents hydrogen or a substituent selected from the group consisting of $C_1$-$C_{24}$alkyl, $C_5$-$C_{12}$cycloalkyl, phenyl, —CHR$_d$—CHR$_e$—C(=O)—O—$R_f$ (C$_1$), wherein
one of $R_d$ and $R_e$ represents methyl and the other one represents methyl and $R_f$ represents hydrogen or $C_1$-$C_{24}$alkyl,

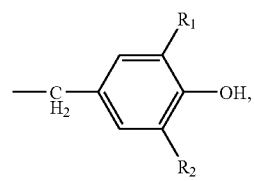
(C$_2$)

wherein $R_1$ and $R_2$ are as defined above, and

—CH$_2$—C(=O)—O—$R_f$ (C$_3$), wherein $R_f$ is as defined above; and,
$Y_2$ represents hydroxy-$C_2$-$C_4$alkyl;
if n represents 2,
m represents zero, Y represents a bivalent group selected from the group consisting of —O—$C_xH_{2x}$—O— wherein x is a numeral from 2 to 20,

—O—(CH$_2$—CH$_2$—O)$_y$—CH$_2$—CH$_2$—O— (E), wherein y is a numeral from 1 to 30,

—O—CH$_2$—CH$_2$—S—CH$_2$—CH$_2$—O—

—O—CH$_2$—CH=CH—CH$_2$—O— (G)

—NH—(CH$_2$)$_z$—NH— (H), wherein z represents zero or a numeral from 2 to 10; and
if n represents 3,
m represents zero and Y represents a trivalent group selected from the group consisting of

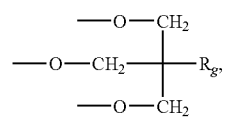
(K)

wherein $R_g$ represents $C_1$-$C_{24}$alkyl or phenyl, and

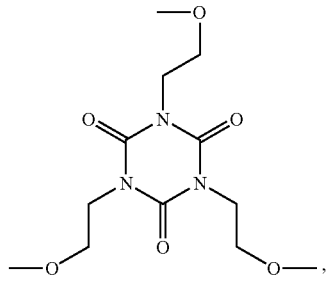
(L)

and, if n represents 4,
m represents zero and Y represents a tetravalent group of the partial formula:

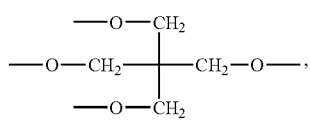
(M)

characterised in that in a compound of the formula:

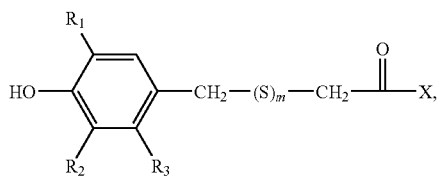
(II)

wherein
$R_1$, $R_2$, $R_3$ and m are as defined above and —X represents $C_1$-$C_4$ alkoxy, the group —X is replaced by enzymatic catalysis with a mono-, bi-, tri- or tetravalent group —Y that corresponds to the value of the numeral n,
if n represents 1 with the monovalent group —O—$Y_1$ or —N(—$Y_2$)$_2$; or,
if n represents 2, with one of the bivalent groups (D), (E), (F), (G) or (H); or,
if n represents 3, with the trivalent group of the partial formulae (K) or (L); or,
if n represents 4, with the tetravalent group of the partial formula (M).

2. A process according to claim 1 for the preparation of a compound (I), wherein
one of $R_1$ and $R_2$ represents methyl, tert-butyl or the group (A), wherein $R_a$ represents hydrogen or chloro, and the other one of $R_1$ and $R_2$ represents tert-butyl;
$R_3$ represents hydrogen;
m represents zero or 1; and
n represents a numeral from 1 to 4; and,
if n represents 1, m represents zero or 1, and Y represents the monovalent groups —O—$Y_1$ or —N(—$Y_2$)$_2$;
if n represents 2, m represents zero, and Y represents the bivalent groups (D), (E), (F), (G) or (H); or,
if n represents 3, m represents zero, and Y represents the trivalent group of the partial formulae (K) or (L); or, if n represents 4, m represents zero, and Y represents the tetravalent group of the partial formula (M), characterised in that the process steps of claim 1 are carried out.

3. A process according to claim 1 for the preparation of a compound (I), wherein one of $R_1$ and $R_2$ represents methyl, tert-butyl or the group (A), wherein $R_a$ represents hydrogen or chloro, and the other one of $R_1$ and $R_2$ represents tert-butyl;

$R_3$ represents hydrogen;

m represents zero or 1; and n represents a numeral from 1 to 4; and, if n represents one, m represents zero or one, and Y represents the monovalent groups —O—$Y_1$ or —N(—$Y_2$)$_2$;

wherein $Y_1$ is selected from the group consisting of $C_5$-$C_{45}$alkyl and $C_3$-$C_{45}$alkyl interrupted by at least one O-heteroatom and $Y_2$ represents hydroxy-$C_2$-$C_4$alkyl; and, if n represents 2, m represents zero, Y represents a bivalent group selected from the group consisting of —O—$C_xH_{2x}$—O— wherein x is a numeral from 2 to 20,

—O—($CH_2$—$CH_2$—O)$_y$—$CH_2$—$CH_2$—O— wherein y is a numeral from 1 to 30,

—O—$CH_2$—$CH_2$—S—$CH_2$—$CH_2$—

—NH—($CH_2$)$_z$—NH—   (H);

wherein z represents zero or a numeral from 2 to 10; and, if n represents 3, m represents zero and Y represents a trivalent group selected from the group consisting of $$\begin{array}{c} —O—CH_2 \\ —O—CH_2—\!\!\!\!\!\!\!\!\!\!\!\!\!\!\!\!\!\!\!\!\!\!\!-\!\!\!-R_g, \\ —O—CH_2 \end{array} \quad (K)$$

wherein $R_g$ represents $C_1$-$C_{24}$alkyl, and (L)

[structure of tris(2-hydroxyethyl) isocyanurate-derived trivalent group]

and, if n represents 4, m represents zero and Y represents a tetravalent group of the partial formula:

$$\begin{array}{c} —O—CH_2 \\ —O—CH_2—\!\!\!\!\!\!\!\!\!\!\!\!\!\!\!\!\!\!\!\!\!\!\!-\!\!\!-CH_2—O—, \\ —O—CH_2 \end{array} \quad (M)$$

characterised in that the process steps of claim 1 are carried out.

4. A process according to claim 1 for the preparation of a compound (I), wherein one of $R_1$ and $R_2$ represents methyl, tert-butyl or the group (A), wherein $R_a$ represents hydrogen or chloro, and the other one of $R_1$ and $R_2$ represents tert-butyl;

$R_3$ represents hydrogen;

m represents zero or 1; and n represents a numeral from 1 to 4; and, if n represents one, Y represents the monovalent groups —O—$Y_1$ or —N(—$Y_2$)$_2$;

wherein $Y_1$ is selected from the group consisting of $C_5$-$C_{20}$alkyl and $C_3$-$C_{20}$alkyl interrupted by at least one O-heteroatom and $Y_2$ represents hydroxy-$C_2$-$C_4$alkyl; and, if n represents 2, m represents zero, Y represents a bivalent group selected from the group consisting of —O—$C_xH_{2x}$—O— wherein x is a numeral from 2 to 10,

—O—($CH_2$—$CH_2$—O)$_y$—$CH_2$—$CH_2$—O— wherein y is a numeral from 1 to 10,

—O—$CH_2$—$CH_2$—S—$CH_2$—$CH_2$—

—NH—($CH_2$)$_z$—NH—   (H);

wherein z represents zero or a numeral from 2 to 10; and, if n represents 3, m represents zero, and Y represents the trivalent group (L); and, if n represents 4, m represents zero and Y represents a tetravalent group (M), characterised in that the process steps of claim 1 are carried out.

5. A process according to claim 1 for the preparation of a compound (I), wherein one of $R_1$ and $R_2$ represents methyl or tert-butyl and the other one of $R_1$ and $R_2$ represents tert-butyl;

$R_3$ represents hydrogen;

m represents zero or 1; and n represents a numeral from 1 to 4; and, if n represents 1, Y represents the monovalent groups —O—$Y_1$ or —N(—$Y_2$)$_2$;

wherein $Y_1$ is selected from the group consisting of $C_5$-$C_{20}$alkyl and $C_3$-$C_{20}$alkyl interrupted by at least one O-heteroatom and $Y_2$ represents hydroxy-$C_2$-$C_4$alkyl; and, if n represents 2, m represents zero, Y represents a bivalent group selected from the group consisting of —O—$C_xH_{2x}$—O— wherein x is a numeral from 2 to 10,

—O—($CH_2$—$CH_2$—O)$_y$—$CH_2$—$CH_2$—O— wherein y is a numeral from 1 to 10,

—O—CH$_2$—CH$_2$—S—CH$_2$—CH$_2$—

—NH—(CH$_2$)$_z$—NH—           (H);

wherein z represents zero or a numeral from 2 to 10; and, if n represents 3, m represents zero, and Y represents the trivalent group (L); and, if n represents 4, m represents zero and Y represents a tetravalent group (M), characterised in that the process steps of claim 1 are carried out.

6. A process according to claim 1 for the preparation of a compound (I), wherein R$_1$ represents tert-butyl;
R$_2$ represents the group (A), wherein R$_a$ represents hydrogen or chloro;
R$_3$ represents hydrogen;
m represents zero;
n represents 1; and
Y represents the monovalent group —O—Y$_1$;
wherein Y$_1$ is selected from the group consisting of C$_5$-C$_{20}$alkyl and C$_3$-C$_{20}$alkyl interrupted by at least one O-heteroatom, characterised in that the process steps of claim 1 are carried out.

7. A process according to claim 1, characterised in that the reactive leaving group —X in a compound (II) is a methoxy group.

8. A process according to claim 1, characterised in that the enzymatic catalysis is carried out with an enzyme selected from the group consisting of esterase, lipase and protease.

9. A process according to claim 1, characterised in that the enzymatic catalysis is carried out with enzymes immobilised on a support material or carrier, to which they are linked chemically or physically.

10. A process according to claim 1, characterised in that the mono-, bi-, tri- or tetravalent group Y that corresponds to the value of the numeral n is derived, if n represents 1, from an alcohol HO—Y$_1$ or an amine HN(—Y$_2$)$_2$;
if n represents 2, from a dihydroxy alcohol selected from the group consisting of HO—C$_x$H$_{2x}$—OH wherein x is a numeral from 2 to 20, HO—(CH$_2$—CH$_2$—O)$_y$—CH$_2$—CH$_2$—OH           (E'), wherein y is a numeral from 1 to 30, HO—CH$_2$—CH$_2$—S—CH$_2$—CH$_2$—OH           (F') and

HO—CH$_2$—CH=CH—CH$_2$—OH from hydrazine or a diamino compound

NH$_2$—(CH$_2$)$_z$—NH$_2$           (H'), wherein z represents zero or a numeral from 2 to 10; and, if n represents 3, from a trihydroxy alcohol Y selected from the group consisting of $$\begin{array}{c} HO-CH_2 \\ HO-CH_2-\!\!\!-\!\!\!-R_g, \\ HO-CH_2 \end{array} \quad (K')$$

wherein R$_g$ represents C$_1$-C$_{24}$alkyl or phenyl, and (L)

[structure of tris(2-hydroxyethyl) isocyanurate]

and, if n represents 4, from pentaerythritol.

\* \* \* \* \*